United States Patent
Kato et al.

(10) Patent No.: US 11,331,353 B2
(45) Date of Patent: May 17, 2022

(54) SLEEP QUALITY IMPROVER

(71) Applicant: KABUSHIKI KAISHA YAKULT HONSHA, Minato-ku (JP)

(72) Inventors: Akito Kato, Minato-ku (JP); Mai Takada, Minato-ku (JP)

(73) Assignee: KABUSHIKI KAISHA YAKULT HONSHA, Minato-ku (JP)

( * ) Notice: Subject to any disclaimer, the term of this patent is extended or adjusted under 35 U.S.C. 154(b) by 0 days.

(21) Appl. No.: 15/123,510

(22) PCT Filed: Mar. 20, 2015

(86) PCT No.: PCT/JP2015/058528
§ 371 (c)(1),
(2) Date: Sep. 2, 2016

(87) PCT Pub. No.: WO2015/146844
PCT Pub. Date: Oct. 1, 2015

(65) Prior Publication Data
US 2017/0071987 A1    Mar. 16, 2017

(30) Foreign Application Priority Data
Mar. 25, 2014 (JP) .............................. JP2014-062377

(51) Int. Cl.
*A61K 35/747* (2015.01)
*A61K 31/685* (2006.01)

(52) U.S. Cl.
CPC .......... *A61K 35/747* (2013.01); *A61K 31/685* (2013.01)

(58) Field of Classification Search
None
See application file for complete search history.

(56) References Cited

U.S. PATENT DOCUMENTS

| | | |
|---|---|---|
| 2001/0051152 A1 | 12/2001 | Krueger et al. |
| 2007/0207134 A1 | 9/2007 | Moriyama et al. |
| 2008/0268065 A1 | 10/2008 | Moriyama et al. |
| 2012/0009163 A1 | 1/2012 | Sawada et al. |
| 2013/0336943 A1 | 12/2013 | Sawada et al. |

FOREIGN PATENT DOCUMENTS

| | | |
|---|---|---|
| EP | 0 937 407 A1 | 8/1999 |
| JP | 2001-270830 A | 10/2001 |
| JP | 2003-517828 A | 6/2003 |
| JP | 2004-141065 A | 5/2004 |
| JP | 2006-62998 A | 3/2006 |
| JP | 2007-70343 A | 3/2007 |
| JP | 2011-36203 A | 2/2011 |
| JP | 2011-193730 A | 10/2011 |
| JP | 2012-17282 A | 1/2012 |

(Continued)

OTHER PUBLICATIONS

GRAS Notice Lactobacillus casei, Mar. 2012.*

(Continued)

*Primary Examiner* — Erin M. Bowers
(74) *Attorney, Agent, or Firm* — Oblon, McClelland, Maier & Neustadt, L.L.P.

(57) ABSTRACT

Provided is a novel agent for improving sleep quality. An agent for improving sleep quality containing, as an active ingredient, bacterial cells of *Lactobacillus casei* and/or a treated product thereof.

5 Claims, 2 Drawing Sheets

(56) References Cited

FOREIGN PATENT DOCUMENTS

| WO | WO 01/45722 A1 | | 6/2001 |
|---|---|---|---|
| WO | 2005/094849 A1 | | 10/2005 |
| WO | WO 2006/128465 | * | 12/2006 |
| WO | 2008/155999 A1 | | 12/2008 |
| WO | WO 2012/065812 | * | 5/2012 |
| WO | WO 2012/170021 A1 | | 12/2012 |

OTHER PUBLICATIONS

GRAS Notice for Lactobacillus casei, published Mar. 2012.*
Office Action dated Aug. 1, 2017 in Japanese Patent Application No. 2016-510303.
"Yakult 400," <URL:http://web.archive.org/web/20130808102947/http://www.yakult.co.jp/products/item0007.html>. Aug. 8, 2013, (with partial English translation) (3 pages).
S. Yamamura, et al., "The effect of *Lactobacillus helveticus* fermented milk on sleep and health perception in elderly subjects," European Journal of Clinical Nutrition, 2009, vol. 63, pp. 100-105.
International Search Report dated May 19, 2015 in PCT/JP2015/058528 filed Mar. 20, 2015.
Extended European Search Report dated May 8, 2018 in European Patent Application No. 15770287.9, 12 pages.

\* cited by examiner

[Figure 1]
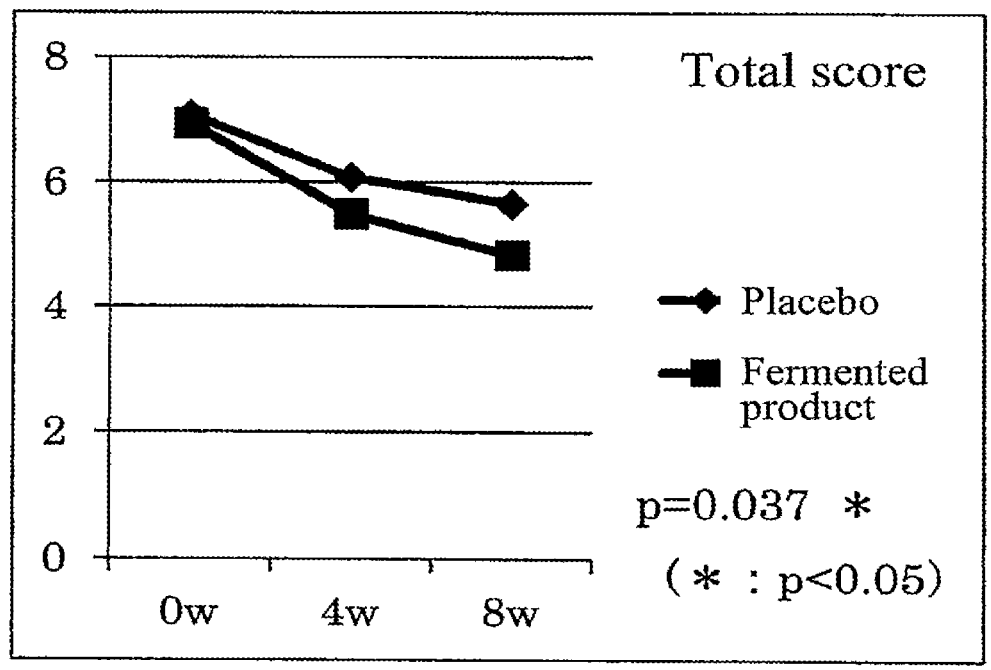
[Figure 2]
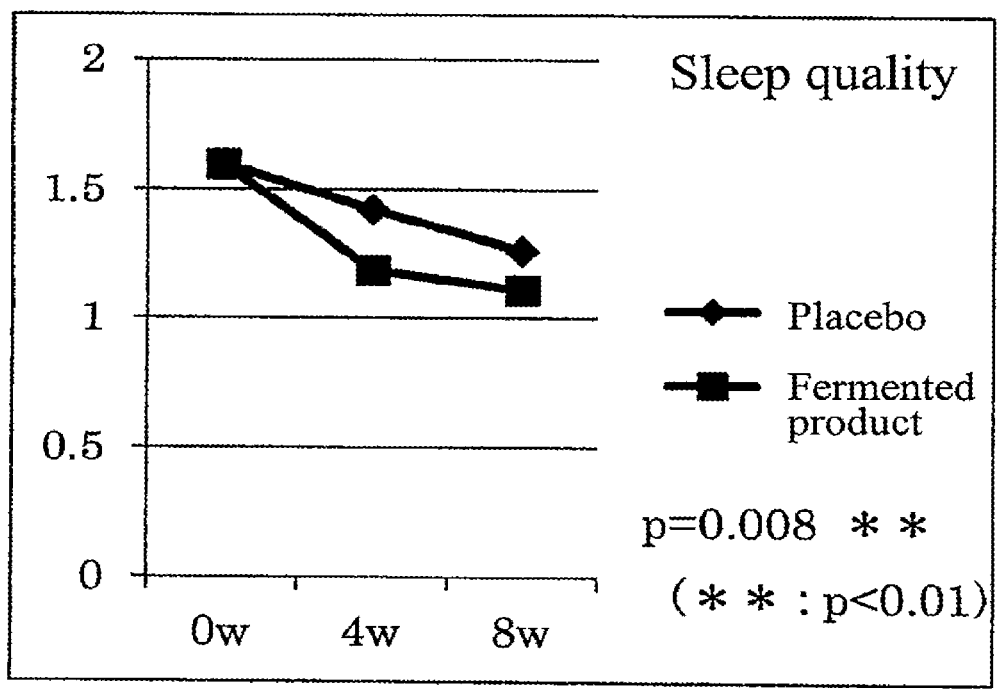

[Figure 3]
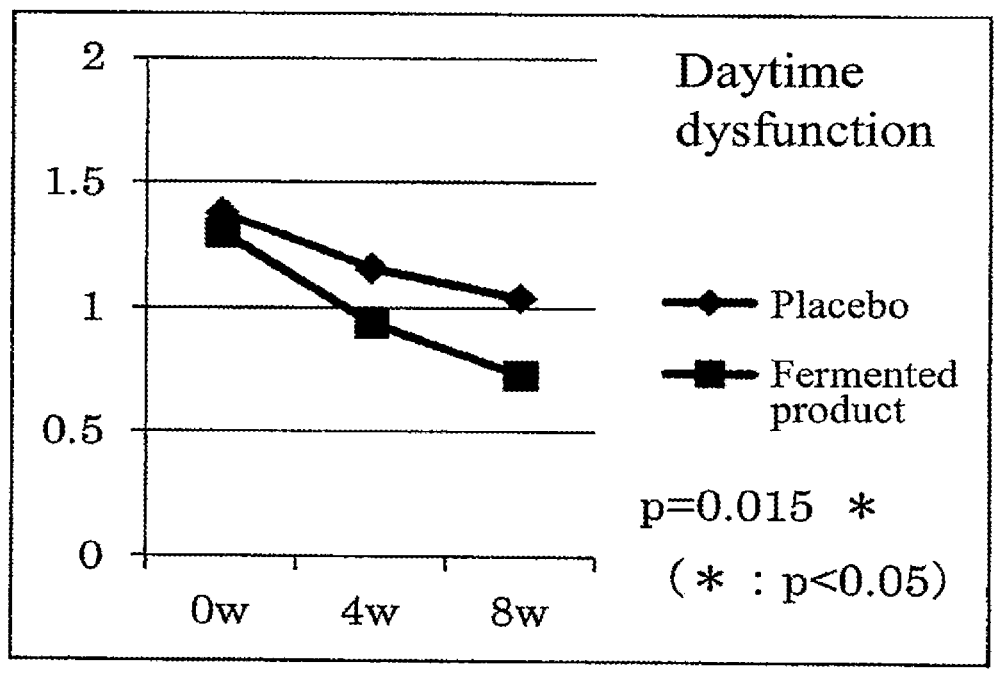
[Figure 4]
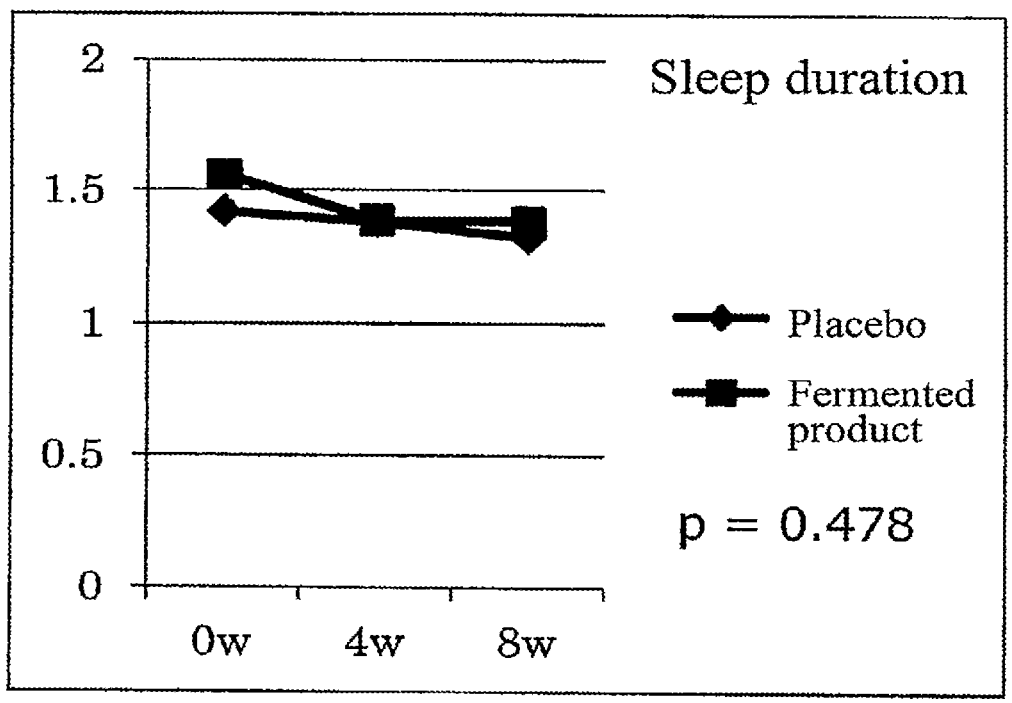

SLEEP QUALITY IMPROVER

FIELD OF THE INVENTION

The present invention relates to an agent for improving sleep quality in people who do not sleep well.

BACKGROUND OF THE INVENTION

In modern society, the number of people who suffer from insomnia or lack of sleep has increased due to stress, unbalanced diet, environment, and the like. The lack of sleep is considered to be a possible cause of obesity, hypertension, poor concentration, depression, diabetes, etc. Thus, it is important to overcome the lack of sleep.

For the purpose of overcoming the lack of sleep, various supplements, as well as sleep-inducing agents, have been recommended. For example, it has been reported that ingestion of amino acid, plant extract, flavor, lactic acid bacteria of the genus *Lactobacillus* or a fermented product thereof, phosphatidylserine (Patent Literatures 1 to 5), and the like improve sleep. However, the effects thereof have not been sufficient.

Moreover, it has also been reported that lactic acid bacteria of the genus *Lactobacillus* and the like do not exhibit an effect of reducing sleep latency (Non Patent Literature 1), and further, it has never been reported that the lactic acid bacteria of the genus *Lactobacillus* and the like exhibit an effect of improving daytime dysfunction (difficulty in staying awake during the day).

CITATION LIST

Patent Literature

Patent Literature 1: JP-A-2003-517828
Patent Literature 2: JP-A-2006-62998
Patent Literature 3: WO 2005/094849
Patent Literature 4: WO 2008/155999
Patent Literature 5: JP-A-2007-70343

Non Patent Literature

Non Patent Literature 1: European Journal of Clinical Nutrition (2009) 63, 100-105

SUMMARY OF THE INVENTION

Problems to be Solved by the Invention

However, as a result of recent studies, it has been revealed that even if a sufficient sleep duration is simply ensured, people may often develop symptoms such as still feeling tired and becoming sleepy in the daytime, and thus that not only sleep duration but also sleep quality is important to overcome the lack of sleep.

Accordingly, the present invention provides a novel agent for improving sleep quality.

Means for Solving the Problems

Hence, the present inventors conducted various studies in order to find an ingredient, which improves not only sleep duration but also sleep quality, and in particular, achieves sleep which does not involve sleepiness in the daytime. As a result, the inventors found that sleep quality, in particular, daytime dysfunction can be significantly improved by ingestion of bacterial cells of *Lactobacillus casei* or a treated product thereof, among bacteria of the genus *Lactobacillus*, thereby completing the present invention.

Specifically, the present invention provides the following [1] to [28]:

[1] An agent for improving sleep quality, comprising, as an active ingredient, bacterial cells of *Lactobacillus casei* and/or a treated product thereof.

[2] The agent for improving sleep quality according to the above [1], wherein the *Lactobacillus casei* is *Lactobacillus casei* YIT 9029 (FERM BP-1366).

[3] The agent for improving sleep quality according to the above [1] or [2], wherein the daily intake is $10^{10}$ cfu or more as the viable bacterial count of *Lactobacillus casei*.

[4] The agent for improving sleep quality according to any one of the above [1] to [3], further comprising phosphatidylserine.

[5] The agent for improving sleep quality according to any one of the above [1] to [4], which is one or more selected from the group consisting of an agent for reducing sleep latency, an agent for improving daytime dysfunction, and an agent for reducing the number of awakenings.

[6] The agent for improving sleep quality according to any one of the above [1] to [5], which is an agent for reducing sleep latency and/or an agent for improving daytime dysfunction.

[7] The agent for improving sleep quality according to any one of the above [1] to [6], which is an agent for improving daytime dysfunction.

[8] Use of bacterial cells of *Lactobacillus casei* and/or a treated product thereof for the production of an agent for improving sleep quality.

[9] The use according to the above [8], wherein the *Lactobacillus casei* is *Lactobacillus casei* YIT 9029 (FERM BP-1366).

[10] The use according to the above [8] or [9], wherein the daily intake is $10^{10}$ cfu or more as the viable bacterial count of *Lactobacillus casei*.

[11] The use according to any one of the above [8] to [10], wherein phosphatidylserine is further used.

[12] The use according to any one of the above [8] to [11], wherein the agent for improving sleep quality is one or more selected from the group consisting of an agent for reducing sleep latency, an agent for improving daytime dysfunction, and an agent for reducing the number of awakenings.

[13] The use according to any one of the above [8] to [12], wherein the agent for improving sleep quality is an agent for reducing sleep latency and/or an agent for improving daytime dysfunction.

[14] The use according to any one of the above [8] to [13], wherein the agent for improving sleep quality is an agent for improving daytime dysfunction.

[15] Bacterial cells of *Lactobacillus casei* and/or a treated product thereof, for use in improving sleep quality.

[16] The bacterial cells and/or a treated product thereof according to the above [15], wherein the *Lactobacillus casei* is *Lactobacillus casei* YIT 9029 (FERM BP-1366).

[17] The bacterial cells and/or a treated product thereof according to the above [15] or [16], wherein the daily intake is $10^{10}$ cfu or more as the viable bacterial count of *Lactobacillus casei*.

[18] The bacterial cells and/or a treated product thereof according to any one of the above [15] to [17], further comprising phosphatidylserine.

[19] The bacterial cells and/or a treated product thereof according to any one of the above [15] to [18], wherein the improvement in sleep quality is one or more selected from the group consisting of a reduction in sleep latency, improvement in daytime dysfunction, and a reduction in the number of awakenings.

[20] The bacterial cells and/or a treated product thereof according to any one of the above [15] to [19], wherein the improvement in sleep quality is a reduction in sleep latency and/or improvement in daytime dysfunction.

[21] The bacterial cells and/or a treated product thereof according to any one of the above [15] to [20], wherein the improvement in sleep quality is improvement in daytime dysfunction.

[22] A method for improving sleep quality, comprising administering an effective amount of bacterial cells of *Lactobacillus casei* and/or a treated product thereof.

[23] The method according to the above [22], wherein the *Lactobacillus casei* is *Lactobacillus casei* YIT 9029 (FERM BP-1366).

[24] The method according to the above [22] or [23], wherein the daily intake is $10^{10}$ cfu or more as the viable bacterial count of *Lactobacillus casei*.

[25] The method according to any one of the above [22] to [24], further comprising administering phosphatidylserine.

[26] The method according to any one of the above [22] to [25], wherein the improvement in sleep quality is one or more selected from the group consisting of a reduction in sleep latency, improvement in daytime dysfunction, and a reduction in the number of awakenings.

[27] The method according to any one of the above [22] to [26], wherein the improvement in sleep quality is a reduction in sleep latency and/or improvement in daytime dysfunction.

[28] The method according to any one of the above [22] to [27], wherein the improvement in sleep quality is improvement in daytime dysfunction.

Effects of the Invention

When *Lactobacillus casei* and/or a treated product thereof is ingested, sleep quality is improved, and in particular, an effect of reducing sleep latency and/or an effect of improving daytime dysfunction are obtained.

BRIEF DESCRIPTION OF THE DRAWINGS

FIG. 1 shows the effect by ingesting *Lactobacillus casei*, with respect to the PSQI total score.

FIG. 2 shows the effect by ingesting *Lactobacillus casei*, with respect to the PSQI sleep quality score.

FIG. 3 shows the effect by ingesting *Lactobacillus casei*, with respect to the PSQI daytime dysfunction score.

FIG. 4 shows the effect by ingesting *Lactobacillus casei*, with respect to the PSQI sleep duration score.

MODES FOR CARRYING OUT THE INVENTION

The active ingredient of the agent for improving sleep quality of the present invention is bacterial cells of *Lactobacillus casei* and/or a treated product thereof.

The strain of *Lactobacillus casei* is not particularly limited, as long as it is *Lactobacillus casei*. Preferred examples of the *Lactobacillus casei* strain include *Lactobacillus casei* YIT 9018 (FERM BP-665), *Lactobacillus casei* YIT 9029 (FERM BP-1366), and *Lactobacillus casei* YIT 10003 (FERM BP-7707). In terms of the effect of improving sleep quality, *Lactobacillus casei* YIT 9029 (FERM BP-1366) is particularly preferable.

In the present invention, the "treated product of bacterial cells" means the bacteria used herein (*Lactobacillus casei*), on which a certain treatment has been performed. The type of the treatment is not particularly limited.

An example of the treated product of *Lactobacillus casei* is a degradation product of bacterial cells or the like. Specific examples include a lysate of *Lactobacillus casei* obtained by ultrasonic waves or the like, an enzyme-treated liquid of *Lactobacillus casei*, and a solid residue obtained by separating the aforementioned products by solid-liquid separation means such as filtration or centrifugation. Moreover, a nucleic acid-containing fraction obtained by lysing *Lactobacillus casei* with a surfactant or the like, followed by precipitation with ethanol or the like, is also included in the treated product of *Lactobacillus casei*. Furthermore, the above described lysate of *Lactobacillus casei* obtained by ultrasonic waves or the like, the above described enzyme-treated liquid of the cells of *Lactobacillus casei*, and the like, which are further subjected to, for example, separation and/or purification treatments, such as separation by various types of chromatography, are also included in the treated product of *Lactobacillus casei*. Further, killed bacterial cells are also included in the treated product of *Lactobacillus casei*, and such killed bacterial cells can be obtained, for example, by a heat treatment, a treatment using an agent such as an antibiotic, a treatment using a chemical substance such as formalin, a treatment using ultraviolet ray, or a treatment using radiation rays such as γ-ray. Among these treatments, an ultrasonic wave treatment, an enzyme treatment, and a heat treatment are particularly preferable.

Among these bacterial cells and the treated products thereof, viable bacterial cells are more preferable, in terms of the effect of improving sleep quality.

The form of the bacterial cells of *Lactobacillus casei* and/or a treated product thereof is not particularly limited, as long as they comprise the bacterial cells or a treated product thereof. In terms of the ease of ingestion, the continuity of ingestion, the effect of improving sleep quality, etc., it is more preferable to take the form of a fermented product comprising *Lactobacillus casei*. Examples of such a fermented product include a fermented milk product, a fermented soymilk product, a fermented fruit juice product, and a fermented plant liquid product. Among these, a fermented milk product is more preferable.

A fermented product comprising *Lactobacillus casei* can be obtained, for example, by culturing *Lactobacillus casei* in a milk component such as animal milk, e.g., cow milk, milk powder, fat milk powder, or powdered skim milk, at a temperature of 30° C. to 40° C. for 5 to 24 hours. Examples of the culture method include static culture, stirring culture, shaking culture, and aeration culture. More preferably, *Lactobacillus casei* alone, or together with other microorganisms, is inoculated and cultured in a sterilized milk medium, and it is then subjected to a homogenization treatment, so as to obtain a fermented milk base. Subsequently, a syrup solution, which has been prepared separately, is added and mixed into the fermented milk base, and the obtained mixture is then homogenized using a homogenizer or the like. Thereafter, a flavor may be further added to the resultant to obtain a final product.

Herein, the term "fermented product" is used to include beverages such as fermented milk and lactic acid bacteria beverages, which are stipulated in Ministerial Ordinance Concerning Compositional Standards, etc. for Milk and Milk Products, hard yogurt, soft yogurt, and plain yogurt. In addition, the fermented product of the present invention includes foods and beverages, in which *Lactobacillus casei* is used, for example, plain type, flavored type, fruit type, sweet taste type, soft type, drink type, solid (hard) type, or frozen type fermented milk, and lactic acid bacteria beverages.

These fermented products may comprise various types of other food materials, as well as sweeteners such as syrup, as necessary. For example, the fermented products may comprise any given ingredients such as various types of carbohydrates, thickeners, emulsifiers, various types of vitamins, antioxidants, and stabilizers. Specific examples of these food materials include: carbohydrates such as sucrose, glucose, fructose, palatinose, trehalose, lactose, xylose, and maltose; sugar alcohols such as sorbitol, xylitol, erythritol, lactitol, palatinit, reduced sugar syrup, and reduced malt sugar syrup; sweeteners with high degree of sweetness, such as aspartame, thaumatin, sucralose, acesulfame K, and stevia; various types of thickeners (stabilizers), such as agar, gelatin, carrageenan, Guar gum, xanthan gum, pectin, locust bean gum, gellan gum, carboxymethyl cellulose, soybean polysaccharides, and propylene glycol alginate; emulsifiers such as sucrose fatty acid ester, glycerin fatty acid ester, polyglycerin fatty acid ester, sorbitan fatty acid ester, and lecithin; milk fats such as cream, butter, and sour cream; acidulants such as citric acid, lactic acid, acetic acid, malic acid, tartaric acid, and gluconic acid; various types of vitamins such as vitamin A, B vitamins, vitamin C, and E vitamins; minerals such as calcium, magnesium, zinc, iron, and manganese; and flavors such as yogurt-based flavor, berry-based flavor, orange-based flavor, Chinese quince-based flavor, Japanese basil-based flavor, citrus-based flavor, apple-based flavor, mint-based flavor, grape-based flavor, apricot-based flavor, pear, custard cream, peach, melon, banana, tropical, herb-based flavor, tea, and coffee.

For the production of fermented products, microorganisms other than *Lactobacillus casei* may also be used in combination. Examples of such microorganisms include: bacteria of the genus *Bifidobacterium*, such as *Bifidobacterium breve, B. longum, B. bifidum, B. animalis, B. suis, B. infantis, B. adolescentis, B. catenulatum, B. pseudocatenulatum, B. lactis,* and *B. globosum*; bacteria of the genus *Lactobacillus*, such as *L. acidophilus, L. plantarum, L. buchneri, L. gallinarum, L. amylovorus, L. brevis, L. rhamnosus, L. kefir, L. crispatus, L. zeae, L. helveticus, L. salivalius, L. gasseri, L. fermentum, L. reuteri, L. crispatus, L. delbrueckii* subsp. *bulgaricus, L. delbrueckii* subsp. *delbrueckii,* and *L. johnsonii*; bacteria of the genus *Streptococcus*, such as *Streptococcus thermophilus*; bacteria of the genus *Lactococcus*, such as *Lactococcus lactis* subsp. *lactis* and *Lactococcus lactis* subsp. *cremoris*; bacteria of the genus *Enterococcus*, such as *Enterococcus faecalis* and *E. faecium*; bacteria of the genus *Bacillus*, such as *Bacillus subtilis*; and yeasts including those belonging to the genus *Saccharomyces*, the genus *Torulaspora*, or the genus *Candida*, such as *Saccharomyces cerevisiae, Torulaspora delbrueckii,* and *Candida kefyr*. When one or more selected from the group consisting of bacteria of the genus *Lactobacillus* other than *Lactobacillus casei*, bacteria of the genus *Streptococcus*, and bacteria of the genus *Lactococcus* are used in combination with *Lactobacillus casei* to produce a fermented product, high palatability is obtained, and thus, it becomes easy to ingest such a fermented product. Thus, the combined use of other microorganisms is preferable.

Moreover, as a fermented product comprising *Lactobacillus casei*, a commercially available product may be used, and fermented milk-based foods and beverages comprising viable bacteria of *Lactobacillus casei*, which are manufactured by Yakult Honsha Co., Ltd., can be preferably used. Specific examples of such fermented milk-based foods and beverages include Yakult products such as "Yakult," "New Yakult," and "Yakult 400," "Joie," "Sofuhl," "Purela," and "Pretio." In particular, the Yakult products are preferably used because these products contain a large number of viable bacteria of *Lactobacillus casei*.

Furthermore, the agent for improving sleep quality of the present invention more preferably comprises phosphatidylserine, as well as the above described ingredients. With regard to the content of phosphatidylserine, the agent for improving sleep quality comprises preferably 100 mg or more of, and more preferably 300 mg or more of phosphatidylserine, as a daily intake.

Such phosphatidylserine may be derived from either animals or plants. It is preferably derived from plants, and in particular, phosphatidylserine derived from soybeans is more preferable.

The bacterial cells of *Lactobacillus casei* or a treated product thereof exhibits an excellent action to improve sleep quality. Examples of the action to improve sleep quality include an effect of reducing sleep latency, an effect of improving daytime dysfunction, and an effect of reducing the number of awakenings. Among others, the bacterial cells of *Lactobacillus casei* or a treated product thereof is particularly excellent in terms of the effect of improving daytime dysfunction.

Herein, the effect of improving daytime dysfunction, which is exhibited by the agent for improving sleep quality of the present invention, is not obtained by simply increasing sleep duration or the like, but is obtained by improving sleep quality itself. Accordingly, the agent for improving sleep quality of the present invention is particularly excellent in that the sleep effect obtained from sleeping per unit time is significantly improved.

The agent for improving sleep quality of the present invention is particularly effective for a human who recognizes the lack of sleep, a human who has difficulty in falling asleep, a human who wakes up in the middle of the sleep, a human who feels sleepy in the daytime, etc.

Herein, the agent for improving sleep quality of the present invention exhibits an excellent action to improve sleep quality on a human who has a poorer sleep state. With regard to the phase "poor sleep state," for example, the PSQI total score before ingestion of the present improving agent is preferably 4 or more points, more preferably 7 or more points, and particularly preferably 8 or more points.

As described above, with regard to the agent for improving sleep quality of the present invention, it is preferable to ingest *Lactobacillus casei* as a fermented product comprising viable bacteria of *Lactobacillus casei*, and the daily intake thereof is preferably $10^5$ cfu or more, more preferably $10^8$ cfu or more, even more preferably $10^{10}$ cfu or more, and particularly preferably $10^{11}$ cfu or more as the viable bacterial count. Moreover, the duration of intake is preferably 5 days or more, more preferably 2 weeks or more, even more preferably 4 weeks or more, and particularly preferably 8 weeks or more.

The agent for improving sleep quality of the present invention can be used via either oral administration or parenteral administration, and oral administration is preferable. Upon administration, a composition comprising an active ingredient is mixed with a solid or liquid pharmaceutical nontoxic carrier, which is suitable for an administration method such as oral administration, intrarectal administration, or injection, and it can be administered in the form of a commonly used pharmaceutical preparation. Examples of such a preparation include: solid preparations such as a tablet, a granule, a powder, and a capsule; liquid preparations such as a solution, a suspension, and an emulsion; and freeze-dried preparations. These preparations can be prepared according to conventional means applied in the pharmaceutical field. Examples of the above described pharmaceutical nontoxic carrier include glucose, lactose, sucrose, starch, mannitol, dextrin, fatty acid glyceride, polyethylene glycol, hydroxyethyl starch, ethylene glycol, polyoxyethylene sorbitan fatty acid ester, amino acid, gelatin, albumin, water, and saline. Moreover, commonly used additives, such as a stabilizer, a moisturizer, an emulsifier, a binder, a tonicity agent, and an excipient, can be appropriately added, as necessary.

As a pharmaceutical preparation, a commercially available preparation may be used. Pharmaceutical preparations comprising viable bacteria of *Lactobacillus casei*, which are manufactured by Yakult Honsha Co., Ltd., can be preferably used. Specific examples of such a commercially available pharmaceutical preparation include "Yakult BL Intestinal Regulator" and "Yakult BL Intestinal Regulator S-Tablet." Moreover, as a pharmaceutical product for medical use, there is "BIOLACTIS POWDER."

EXAMPLES

Hereinafter, the present invention will be described more in detail in the following Examples.

Production Example 1

Production of Fermented Milk Product Containing *Lactobacillus Casei*

Syrup was mixed into a solution of powdered skim milk, into which *Lactobacillus casei* strain YIT 9029 had been inoculated, followed by fermentation at 37° C., and thereafter, flavor was added to the mixture. Subsequently, the thus obtained mixture was homogenized, and the resultant was then filled into a container, so as to obtain a fermented product. The number of bacteria of *Lactobacillus casei* in 100 mL of the fermented product was $10^{11}$ cfu.

On the other hand, as a placebo, an unfermented product, which did not contain *Lactobacillus casei* and to which lactic acid in an amount corresponding to that in the fermented product had been added to adjust the flavor, was used. It is to be noted that, regarding other compositions, the unfermented product had the same compositions as those of the fermented product.

Test Example 1

One hundred male and female subjects in their 30s to 40s (50 subjects in a placebo group and 50 subjects in a fermented product group), who had a slightly high depression score (Depression Subscale T score: 55 to 75) in the Profile of Mood States (POMS), were allowed to ingest the placebo or the fermented product produced in Production Example 1, at a daily intake of one bottle (100 mL) per day, for 8 weeks. Before initiation of the ingestion, and 4 weeks and 8 weeks after initiation of the ingestion, they were allowed to answer a questionnaire regarding sleep state (PSQI; Pittsburgh Sleep Quality Index), and were then evaluated.

Herein, PSQI has been known as a method for clinically diagnosing sleep quality, and according to this method, sleep quality, daytime dysfunction (daytime sleepiness), and the like can be evaluated. It is to be noted that the average of the PSQI total score of all the subjects, before ingestion, was 7.0 points, and thus, they were considered to be a subject population having not only a high depression score, but also a poor sleep state. The administration effect was analyzed by an analysis of covariance, in which the value before administration was defined as a covariate, and the p value is shown in FIG. 1 to FIG. 4.

As a result, as shown in FIG. 1 to FIG. 3, it was demonstrated that the PSQI total score was significantly improved throughout the ingestion period in the group which ingested *Lactobacillus casei* (p<0.05), and that the sleep was improved. In addition, it was revealed that among the effects obtained by ingestion of *Lactobacillus casei*, the effect of improving sleep quality and the effect of improving daytime dysfunction were particularly remarkable. These improving effects were also significant throughout the ingestion period (sleep quality: p<0.01; daytime dysfunction: p<0.05).

Herein, as shown in FIG. 4, although the sleep duration score of the group which ingested *Lactobacillus casei* was equivalent to that of the group which ingested the placebo, the aforementioned excellent effects were obtained. Accordingly, it was confirmed that the effects of the agent for improving sleep quality of the present invention are not exhibited by a simple increase in sleep duration, etc., but are caused by improvement in sleep quality itself, and that the sleep effect obtained from sleeping per unit time is significantly improved.

Test Example 2

Sixteen male and female subjects in their 20s to 40s, who were subjectively dissatisfied with sleep (PSQI score: 4 to 11 points; average: 7.4 points), were divided into two groups. The two groups were allowed to ingest a gelatin soft capsule (Supplism PS; manufactured by Yakult Health Foods Co., Ltd.) containing 300 mg of PS (phosphatidylserine) or a gelatin soft capsule containing a placebo (refined soybean oil), in each different order, in two administration periods each consisting of 5 days separated by a washout period of 9 days. Thereafter, after a washout period of further 9 days, the two groups were allowed to ingest 300 mg of PS (phosphatidylserine)+a fermented milk product (Yakult 400 (Y400); manufactured by Yakult Honsha Co., Ltd.) containing *Lactobacillus casei* ($4 \times 10^{10}$ cfu) for 5 days. The subjective sleep quality during the sample ingestion period was evaluated using a questionnaire regarding sleep. The administration effect was judged by a test regarding difference (Wilcoxon test) from the placebo ingestion period.

As a result, in the analysis targeting all of the subjects (Table 1), both the number of awakenings (number) (the number of awakenings in the middle of the sleep) and sleep latency (minute) (a time required for falling asleep from wakefulness) were decreased in the PS ingestion period, but a statistically significant difference was not found. However, in the ingestion period of PS+a fermented milk product (Yakult 400 (Y400)) containing *Lactobacillus casei*, both the number of awakenings (number) and sleep latency (minute) were further decreased, and the combined effects of PS and *Lactobacillus casei* were confirmed. In particular, regarding the number of awakenings (number), a significant difference from the placebo ingestion period was observed. Moreover, the subjects were divided into two groups according to the PSQI total score before ingestion, namely, the upper half of the PSQI total score before ingestion (8 or more points) and the lower half thereof (less than 8 points). As a result, it was revealed that, in a group having a high PSQI total score before ingestion (having a poorer sleep state), the degree of decreases in the number of awakenings (number) and the sleep latency (minute) became larger in the ingestion period of PS (phosphatidylserine)+a fermented milk product (Yakult 400 (Y400)) containing *Lactobacillus casei*, and thus that the effect of reducing the number of awakenings and the effect of reducing sleep latency were further clearly excellent (Table 2). In particular, regarding the number of awakenings (number), a significant effect of reducing the number of awakenings to half or less as compared with that in the placebo ingestion period was confirmed.

TABLE 1

| Analysis results of all subjects (n = 16) | | | |
|---|---|---|---|
| | Placebo | PS | PS + Y400 |
| Number of awakenings (number) | 0.9 ± 0.7 | 0.8 ± 0.8 | 0.6 ± 0.9* |
| Sleep latency (minutes) | 24.2 ± 16.5 | 22.0 ± 12.4 | 19.5 ± 12.7 |

Mean value ± standard deviation, *p < 0.05

TABLE 2

| Analysis of group with poor sleep state (PSQI total score ≥8) (n = 8) | | | |
|---|---|---|---|
| | Placebo | PS | PS + Y400 |
| Number of awakenings (number) | 0.7 ± 0.4 | 0.5 ± 0.7 | 0.3 ± 0.4# |

TABLE 2-continued

| Analysis of group with poor sleep state (PSQI total score ≥8) (n = 8) | | | |
|---|---|---|---|
| | Placebo | PS | PS + Y400 |
| Sleep latency (minutes) | 28.1 ± 16.2 | 24.3 ± 12.2 | 21.1 ± 11.0 |

Mean value ± standard deviation, #p < 0.1

The invention claimed is:

1. A method for improving sleep quality, comprising identifying a subject in need thereof;
administering to the identified subject a fermented product for at least 5 days, the fermented product comprising an effective amount of bacterial cells of *Lactobacillus casei* YIT 9029 (FERM BP-1366),
wherein a daily intake is $10^{10}$ cfu or more as the viable bacterial count of *Lactobacillus casei*; and
wherein the improvement in sleep quality is defined by a number of awakenings of not more than about 0.7 and/or by sleep latency less than about 22 minutes.

2. The method according to claim 1, further comprising administering phosphatidylserine.

3. The method according to claim 1, wherein the fermented product is a fermented milk product, a fermented soymilk product, a fermented fruit juice product, and a fermented plant liquid product.

4. The method according to claim 3, wherein the fermented product is a fermented milk product.

5. The method according to claim 1, wherein the subject recognizes lack of sleep, difficulty falling asleep, wakes up in the middle of sleep or feels sleepy during the day.

* * * * *